United States Patent [19]

Aragones

[11] Patent Number: 5,694,449
[45] Date of Patent: Dec. 2, 1997

[54] METHOD AND SYSTEM FOR DETECTING AND CORRECTING ERRONEOUS EXPOSURES GENERATED DURING X-RAY IMAGING

[75] Inventor: James Kenneth Aragones, Clifton Park, N.Y.

[73] Assignee: General Electric Company, Schenectady, N.Y.

[21] Appl. No.: 650,677

[22] Filed: May 20, 1996

[51] Int. Cl.$^6$ .................................................... H05G 1/44
[52] U.S. Cl. ........................................ 378/115; 378/105
[58] Field of Search ................................. 378/108, 109, 378/110, 111, 112, 115, 116, 117, 95, 96, 97

[56] References Cited

U.S. PATENT DOCUMENTS

| | | | |
|---|---|---|---|
| 4,097,741 | 6/1978 | Pfeiler et al. | 378/116 X |
| 4,119,856 | 10/1978 | Franke | 378/108 X |
| 5,319,696 | 6/1994 | Abel-Malek et al. | 378/108 X |

*Primary Examiner*—David P. Porta
*Attorney, Agent, or Firm*—David C. Goldman; Marvin Snyder

[57] ABSTRACT

The present invention discloses a method and system for detecting and correcting an erroneous exposure generated during x-ray imaging of a patient. In the present invention, x-ray imaging settings for imaging the patient are selected. X-ray beam quality and x-ray quantity values are generated from the selected x-ray imaging settings. An exposure rate is predicted from the x-ray beam quality and x-ray quantity values. The patient is then exposed to an x-ray beam having the generated x-ray beam quality and x-ray quantity values. The total exposure is then determined and compared to the predicted exposure rate. The comparison is then used to determine if the patient is being exposed at an erroneous level. If the exposure is at a correct level, then the exposure is completed. However, if the exposure is not at a correct level, then the exposure is stopped and adjusted to a new exposure level.

20 Claims, 6 Drawing Sheets

| PART | VIEW | ADULT PATIENT SIZE | SUG. kVp | ACTUAL mAs | SOURCE IMAGE DISTANCE |
|---|---|---|---|---|---|
| CHEST (NON GRID) | PA/AP UPR SCREEN | SMALL | 80 | 2 | 72"(1.8m) |
| CHEST (NON GRID) | SCREEN | AVERAGE | 85 | 4 | 72"(1.8m) |
| CHEST (NON GRID) | | LARGE | 90 | 6 | 72"(1.8m) |
| | AP UPN SCREEN | SMALL | 70 | 2 | 40"(1.0m) |
| | | AVERAGE | 75 | 3 | 40"(1.0m) |
| | | LARGE | 85 | 4 | 40"(1.0m) |
| | AP FLAT SCREEN | SMALL | 75 | 2 | 54"(1.4m) |
| | | AVERAGE | 80 | 3 | 54"(1.4m) |
| | | LARGE | 85 | 4 | 54"(1.4m) |
| CHEST NEW BORN | AP SCREEN | | 65 | 0.5 | 40"(1.0m) |
| | LAT SCREEN | | 65-70 | 1 | 40"(1.0m) |
| ABDOMEN | AP GRID | AVERAGE | 70 | 64 | 44"(1.1m) |
| ANKLE | AP SCREEN | AVERAGE | 55 | 2.5 | 40"(1.0m) |
| | LAT SCREEN | AVERAGE | 55 | 2 | 40"(1.0m) |
| CERVICAL SPINE | AP SCREEN | AVERAGE | 60 | 8 | 40"(1.0m) |
| | LAT/OPL SCREEN | AVERAGE | 65 | 14 | 72"(1.8m) |
| ELBOW | AP SCREEN | AVERAGE | 55 | 3 | 40"(1.0m) |
| | LAT SCREEN | AVERAGE | 60 | 3 | 40"(1.0m) |
| FEMUR | AP/LAT SCREEN | AVERAGE | 56 | 10 | 40"(1.0m) |
| FOOT | AP SCREEN | AVERAGE | 52 | 1.5 | 40"(1.0m) |
| HAND/WRIST | PA SCREEN | AVERAGE | 50 | 1 | 40"(1.0m) |
| | LAT SCREEN | AVERAGE | 56 | 1.5 | 40"(1.0m) |
| HUMERUS | AP/LAT SCREEN | AVERAGE | 55 | 5 | 40"(1.0m) |
| KNEE | AP SCREEN | AVERAGE | 55 | 5 | 40"(1.0m) |
| | LAT SCREEN | AVERAGE | 55 | 3.2 | 40"(1.0m) |
| LUMBAR SPINE | AP GRID | AVERAGE | 75 | 50 | 44"(1.1m) |
| | LAT GRID | AVERAGE | 85 | 175 | 44"(1.1m) |
| PELVIS/HIP | AP SCREEN | AVERAGE | 65 | 25 | 40"(1.0m) |
| | AP GRID | AVERAGE | 70 | 60 | 40"(1.0m) |
| | LAT GRID | AVERAGE | 80 | 85 | 44"(1.1m) |
| SHOULDER / CLAVICLE | AP SCREEN | AVERAGE | 55 | 5 | 40"(1.0m) |
| SKULL | AP SCREEN | AVERAGE | 80 | 18 | 40"(1.0m) |
| | LAT SCREEN | AVERAGE | 56 | 10 | 40"(1.0m) |
| | AP GRID | AVERAGE | 75 | 20 | 40"(1.0m) |
| | LAT GRID | AVERAGE | 65 | 10 | 40"(1.0m) |

*fig. 2*

METHOD AND SYSTEM FOR DETECTING AND CORRECTING ERRONEOUS EXPOSURES GENERATED DURING X-RAY IMAGING

BACKGROUND OF THE INVENTION

The present invention relates generally to radiography, and more particularly to improving image quality by detecting and correcting erroneous exposures generated during x-ray imaging.

In x-ray imaging systems such as a medical system, an x-ray tube is used to irradiate a patient with a beam of x-rays. The x-rays pass through a patient, exposing a photographic film stored in a cassette. The photographic film is generally comprised of a sheet of translucent supporting material coated on one or both sides with a photosensitized emulsion. The photosensitized emulsion is activated by exposure to photons of different wavelengths within the electromagnetic spectrum, including the visible light band and the x-ray band. Activation of the photosensitized emulsion creates a latent image on the emulsion. The latent image appears on the film as the relative darkening of the emulsion proportional to the amount of exposure. A part of the body interposed between the beam of x-rays and the film absorbs the x-rays in variable degrees depending on the internal composition of the part being x-rayed. More specifically, x-ray transmission through the part is affected by its thickness and material composition, as well as the quality of the x-ray beam striking the object. High energy x-rays penetrate further through the part, while low energy x-rays are easily absorbed. After the latent image has been created, it is then developed by bringing a developer material in contact with the image. Developing the latent image makes it visible and allows a radiologist to make a diagnosis based on the image.

For each exposure that is taken, the radiologist or x-ray technician selects both the quality of the x-ray beam and the amount of x-rays to be generated. In particular, the quality of the x-ray beam is selected by varying voltage and filtration, while the amount of x-rays generated is selected by varying current and duration of the exposure. Both the quality of the x-ray beam and the amount of x-rays generated has a direct influence on the quality of the x-ray image, which in turn effects the accuracy of the diagnosis made by the radiologist.

Currently, there are two procedures that assure exposure during medical x-ray imaging. The first procedure is an automated method of selecting x-ray settings based on exposure guide tables. In this procedure, the operator chooses the anatomic view of how a patient's body part is to be imaged and the estimated size of the patient. The exposure guide tables are then used to provide a value for the beam quality and the amount of x-rays for the desired anatomical view and approximate patient size. Once the settings are made, no further changes are made and the image is taken at these settings. However, if there was an error in the settings, placement, etc., then there is no way to detect it until the film has been developed. Another problem with the exposure guide tables is that these tables give suggested settings only for patients of approximately average composition. Excessively thin, muscular, and obese patients fall outside the range of these tables. The second procedure, known as automatic exposure control, utilizes a sensor such as an ion chamber placed behind the image plane to monitor the amount of x-rays passing through the film. When a sufficient amount of x-rays have passed through the sensor to achieve an acceptable film density, the exposure is terminated. While the automatic exposure control procedure does control the film density over the sensor quite well, it does not change the quality of the x-rays being absorbed by the patient. Another problem is that this procedure does not compensate for grossly incorrect setting errors. For example, it is fairly common to misplace the sensor underneath the spinal column or outside the rib cage on obese patients during a lung exposure. Both locations will have vastly different x-ray absorption characteristics than if placed under the lung.

Since both of the above exposure selection procedures are incapable of detecting incorrect images until after the exposure is taken and the film is developed, exposures may have to be repeated several times. In addition, both exposure selection procedures are incapable of selecting beam quality based on measurements from the actual patient and anatomy being imaged, which may necessitate additional exposures. More exposures results in decreased productivity, more costs, and more dosage to the patient. Therefore, there is a need for detecting and correcting incorrect exposures in order to improve image quality. By improving image quality on the initial exposure, the need for retakes will decrease, which will increase productivity, patient care and decrease cost and the amount of x-ray dosage to the patient.

SUMMARY OF THE INVENTION

Therefore, it is a primary objective of the present invention to provide a method and system for detecting and correcting erroneous exposures during medical x-ray imaging.

Another object of the present invention is to improve image quality generated during medical x-ray imaging.

Thus, in accordance with the present invention, there is provided a method and a system for detecting an erroneous exposure generated during x-ray imaging of a patient. In the present invention, x-ray imaging settings for imaging the patient are selected. X-ray beam quality and x-ray quantity values are generated from the selected x-ray imaging settings. An exposure rate is predicted from the x-ray beam quality and x-ray quantity values. The patient is then exposed to an x-ray beam having the generated x-ray beam quality and x-ray quantity values. The total exposure rate is determined and then compared to the predicted exposure rate. The comparison is then used to determine if the patient is being exposed at an erroneous level.

In accordance with another embodiment of the present invention, there is provided a method and system for correcting an erroneous exposure generated during x-ray imaging of a patient. In the present invention, x-ray imaging settings for imaging the patient are selected. X-ray beam quality and x-ray quantity values are generated from the selected x-ray imaging settings. An exposure rate is predicted from the x-ray beam quality and x-ray quantity values. The patient is then exposed to an x-ray beam having the generated x-ray beam quality and x-ray quantity values. The total exposure rate is determined and then compared to the predicted exposure rate. The comparison is then used to determine if the patient is being exposed at a correct level. If the exposure is at a correct level, then the exposure is completed. However, if the exposure is not at a correct level, then the exposure is adjusted to a new exposure level.

While the present invention will hereinafter be described in connection with a preferred embodiment and method of use, it will be understood that it is not intended to limit the invention to this embodiment. Instead, it is intended to cover all alternatives, modifications and equivalents as may be

BRIEF DESCRIPTION OF THE DRAWINGS

FIG. 2 is an example of an exposure guide table according to the present invention;

DETAILED DESCRIPTION OF THE PRESENT INVENTION

Figure 1:
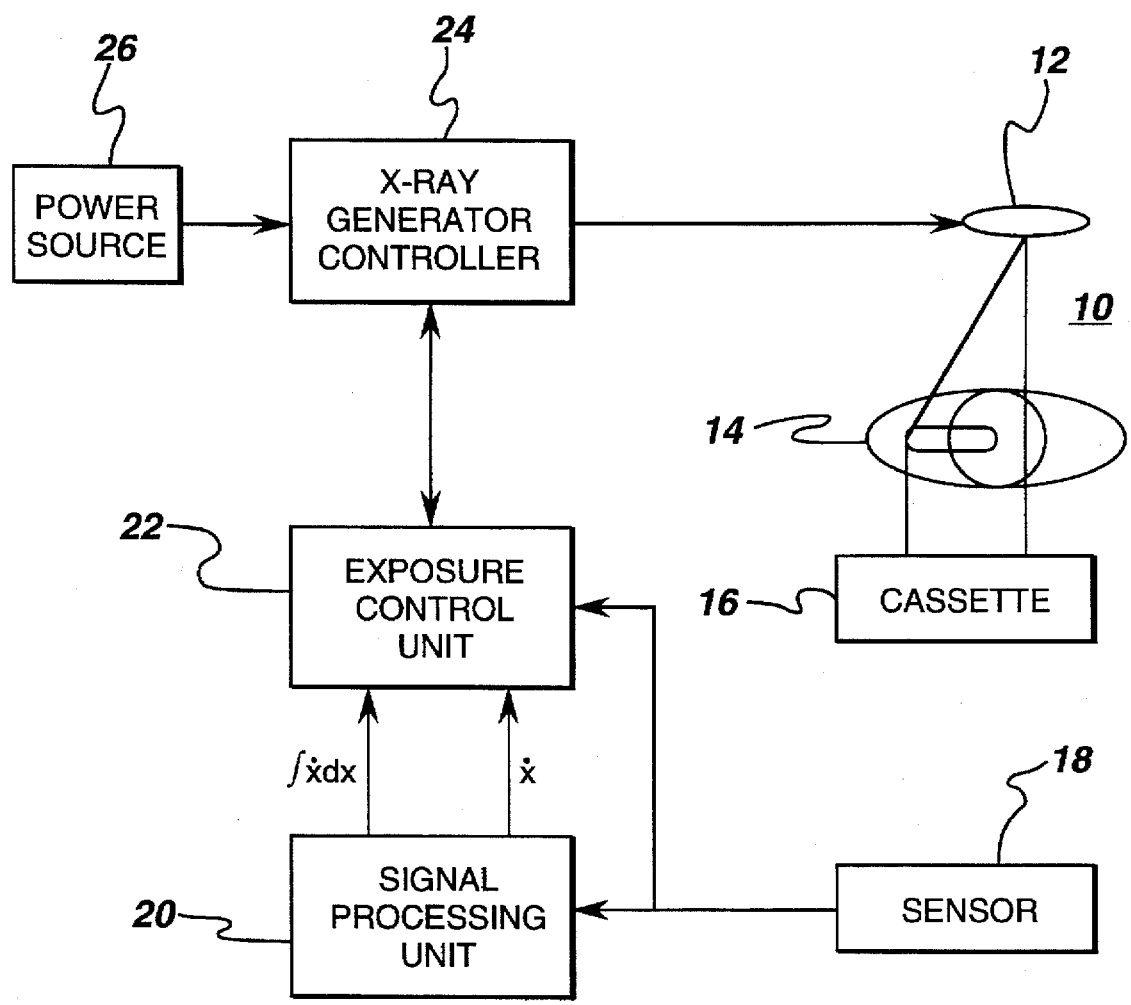
FIG. 1 shows a schematic diagram of a medical radiological x-ray system according to the present invention.

FIG. 1 shows a schematic diagram of a medical radiological x-ray system 10 according to the present invention. Although the present invention is described with reference to a medical radiological system, it can be used in other applications that use x-ray imaging systems such as nondestructive testing and veterinary radiological x-ray systems. In the medical radiological x-ray system 10, an x-ray tube 12 irradiates a particular part of a patient 14 with a beam of x-rays. The x-rays pass through the patient, exposing a photographic film stored in a cassette 16. The photographic film is generally comprised of a sheet of translucent supporting material coated on one or both sides with a photosensitized emulsion. A sensor 18 such as an ion chamber is placed behind the cassette 16 to monitor the amount of x-rays passing through the film. The sensor 18 outputs the amount of photons passing through the film to a signal processing unit 20 and an exposure control unit 22. The signal processing unit 20 amplifies and integrates the amount of photons to produce a summation value represented by $\int xdx$ and $\dot{x}$. The exposure control unit 22, such as a processor, receives the summation value from the signal processing unit 20 and the output from the sensor 18 and uses the techniques described below in further detail to detect and correct erroneous exposures. The exposure control unit 22 then instructs an x-ray generator controller 24 powered by a power source 26 to either change the amount of voltage and current being provided to the x-ray tube 12 or when to stop providing the present amount of voltage and current being sent to the x-ray tube.

In the present invention, the amount of x-rays sent from the x-ray tube 12 is controlled by the x-ray generator controller 24. X-ray imaging settings are selected by a radiologist or a x-ray technician and are based on exposure guide tables. Prior to imaging a patient, the radiologist or x-ray technician chooses the anatomic view to be imaged and estimates the size of the patient. The exposure guide tables are then examined and used to provide a value for the beam quality, $kV_p$, and the amount of x-rays, mAs, for the desired anatomical view and approximate patient size. An example of an exposure guide table is shown in FIG. 2. For example, if a chest is to be x-rayed, and the radiologist or x-ray technician chooses the upright anterior/posterior (AP) anatomic view with a screen and determines that the patient is of average size, then the exposure guide table suggests that 75 $kV_p$ and 3 mAs be used as values for the beam quality and the amount of x-rays, respectively.

Figure 3A:
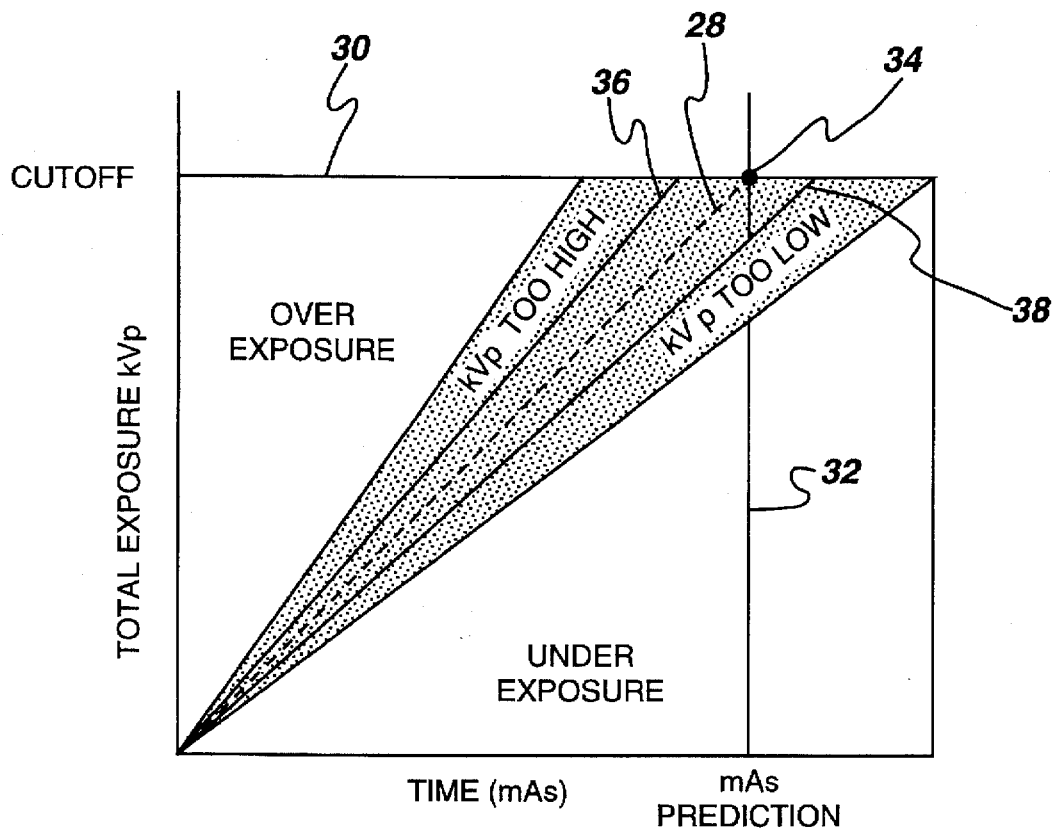
FIGS. 3a-3b are graphs showing the relationship between total exposure and time and exposure rate and time, respectively.
Figure 3B:
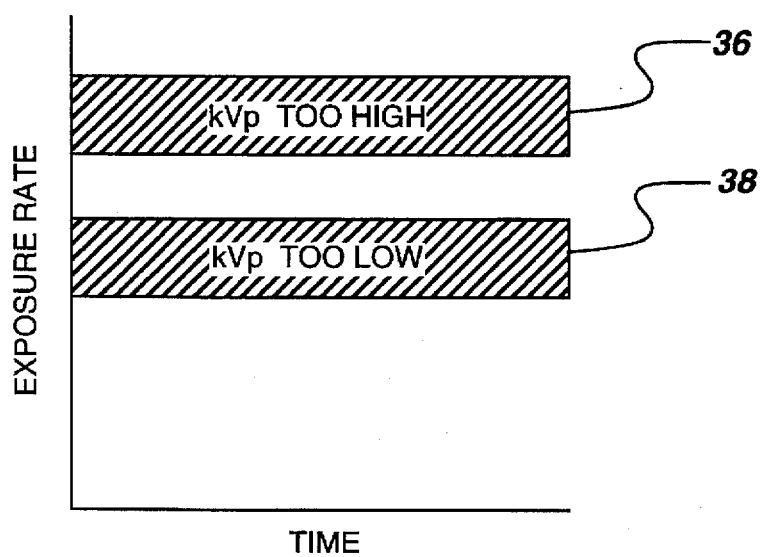

FIG. 3a is graph showing the relationship between total exposure and time with the suggested $kV_p$ and mAs values used as cutoffs. The graph shows how film exposure increases linearly during an ideal x-ray procedure as shown by an optimum trajectory line 28. As the time increases so does the exposure of x-rays. Eventually, the x-ray tube 12 is shut off when the exposure reaches the suggested $kV_p$ value as shown by line 30. In addition, the graph shows a mAs value suggested from an exposure guide table which is used for exposure duration as shown by line 32. In the ideal case, all three of these lines intersect at a single point 34, indicating that the exposure is on track. Encompassing the point 34 are tolerance lines 36 and 38, which indicate the degree of tolerance that will still maintain the exposure on track. FIG. 3b is a graph showing the relationship between exposure rate, which is the derivative of total exposure and time. If there is an error in selecting the anatomic view or estimating the patient size or a misalignment of the sensor, then these lines will no longer intersect at a single point. Any one of these errors will cause the film to be either overexposed or underexposed and may cause overexposure to the patient. In order to account for these errors, the erroneous exposure needs to be detected and corrected to provide the proper amount of tube voltage.

Typically, most of the erroneous exposures are due to operator error. For example, the radiologist or the x-ray technician may misread the exposure guide tables or may incorrectly estimate the patient size. Another common source of error is that there may be a misalignment between the x-ray source, the patient, the cassette, and the sensor. As mentioned above, these errors will lead to either the underexposure or the overexposure of the x-ray film, necessitating that another exposure be made at a later date. These erroneous exposure not only decrease productivity and increase operating costs, but also hinders patient care by increasing diagnosis time, increases the total x-ray dose to the patient, and increases patient handling.

Figure 4:
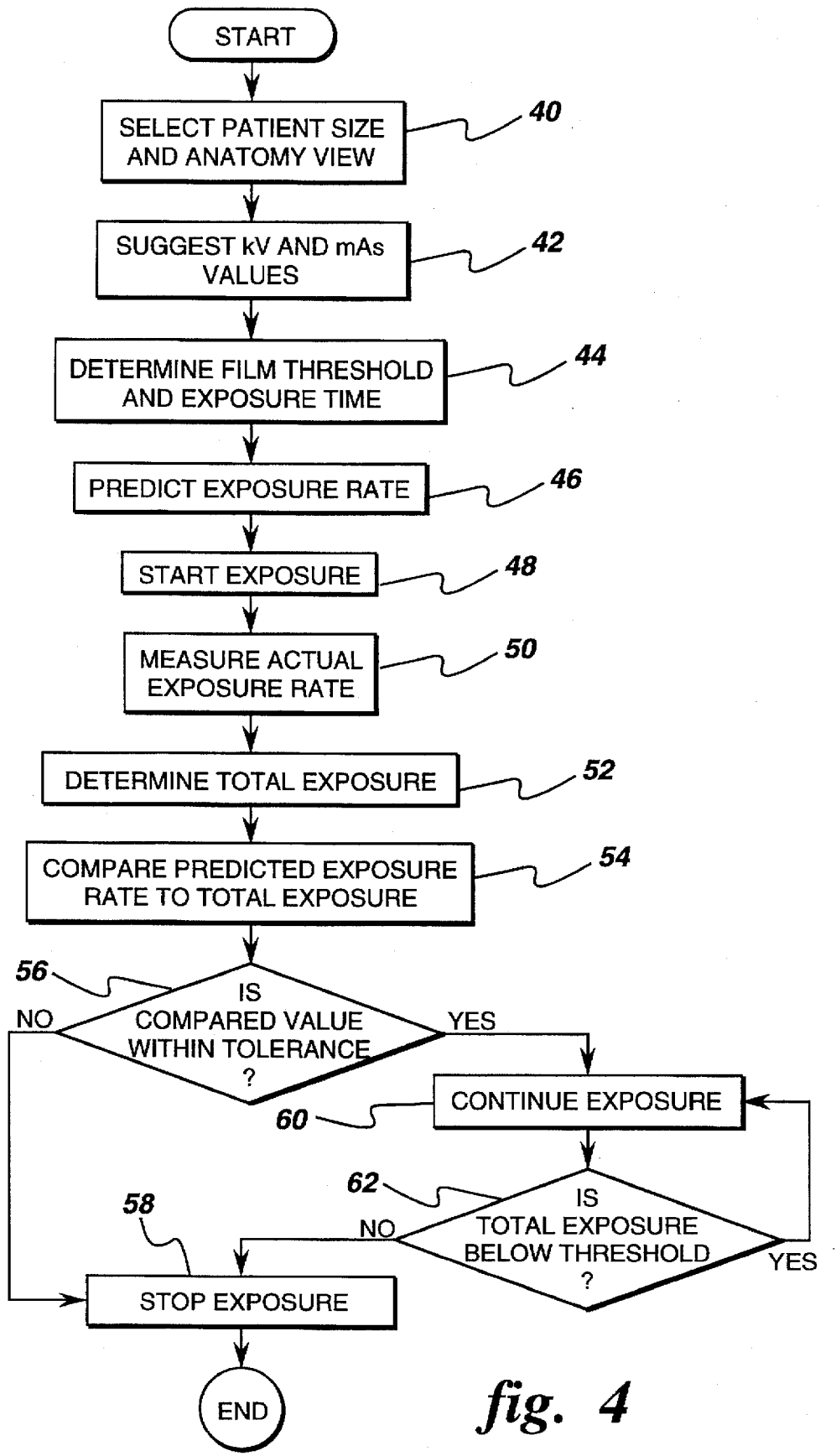
FIG. 4 is a flow chart describing the operation of detecting erroneous exposures according to the present invention.

The present invention is able to detect either an overexposed or an underexposed condition by tracking the total exposure rate of the patient and comparing it to a predicted exposure rate. FIG. 4 describes the series of steps performed by the exposure control unit 22 for detecting erroneous exposures. In this embodiment, the operation is initiated at 40 where the radiologist or x-ray technician selects the anatomic view to be imaged and estimates the size of the patient. An illustrative list of possible anatomic views for different parts of the body is shown in FIG. 2. After the anatomic view and patient size has been selected an exposure guide table such as the one in FIG. 2 is used at 42 to suggest a value for the beam quality, kV, and the amount of x-rays, mAs. For example, if an ankle is to be x-rayed, and the radiologist or x-ray technician chooses the anterior/posterior (AP) anatomic view with a screen and determines that the patient is of average size, then the exposure guide table would suggest that 55 $kV_p$ and 2.5 mAs be used as values for the beam quality and the amount of x-rays, respectively. At 44, the film threshold (i.e., brightness) and exposure time is determined. In particular, the brightness value is determined from the suggested $kV_p$ value and the film type, while the exposure time is determined from the suggested mAs value and the current being provided by the x-ray generator controller 24. Next, the predicted exposure rate is determined at 46 by dividing the brightness by the exposure time. The patient is then exposed to an x-ray beam at 48 having the suggested x-ray beam quality (kV) and x-ray quantity (mAs) values. The actual exposure rate to the patient is then measured at 50. The actual exposure rate is then integrated at 52 to determine the total exposure, which is compared to the predicted exposure rate at 54. The compared value is then used to determine if the exposure of the patient is within a predetermined tolerance. If the compared value is not within the predetermined tolerance at 56, then the exposure is stopped at 58 and the operator is signaled to recheck the x-ray settings. However, if the compared value is within the predetermined tolerance at 56, then the exposure is continued at 60 and the total exposure is compared to a predetermined threshold value at 62. If the total exposure is less than the predetermined threshold, then the exposure continues until the total exposure is equal to the predetermined threshold. Once the total exposure is equal to the predetermined threshold then the exposure is stopped at 58 and an image on the film is recorded.

Figure 5:
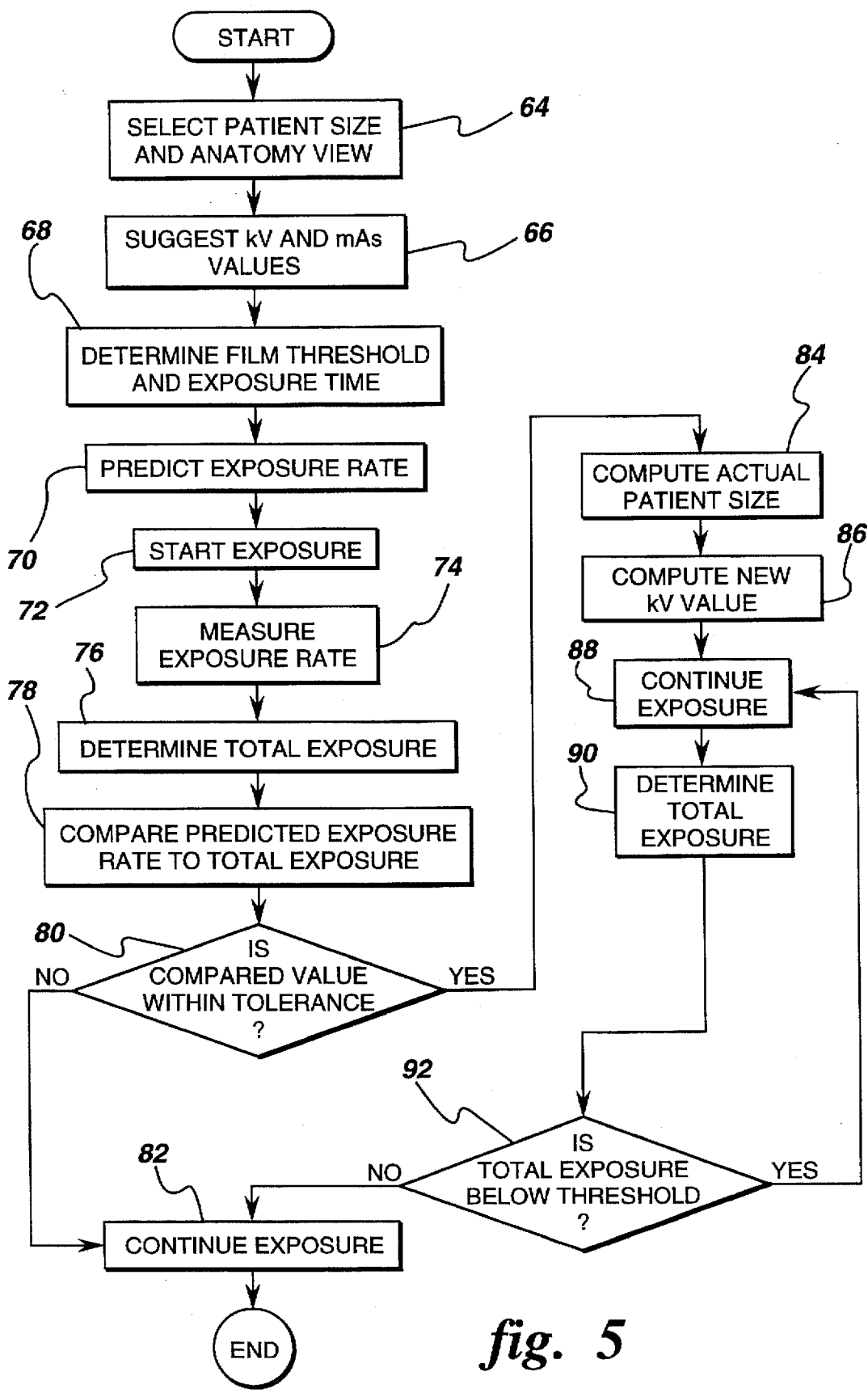
FIG. 5 is a flow chart describing the operation of correcting erroneous exposures according to the present invention.

In addition to detecting erroneous exposures, the present invention is able to correct these exposures by quickly suggesting a new voltage value (kV) and adjusting the x-ray generator 24 by the suggested amount. FIG. 5 sets forth the operation performed by the exposure control unit 22 to correct erroneous exposures. In this embodiment, the radiologist or x-ray technician selects the anatomic view to be imaged and estimates the size of the patient at 64. After the anatomic view and patient size has been selected an exposure guide table such as the one in FIG. 2 is used at 66 to suggest a value for the beam quality (kV) and the amount of x-rays (mAs). At 68, the film threshold (i.e., brightness) and exposure time is determined. Next, the predicted exposure rate is determined at 70 by dividing the brightness by the exposure time. The patient is then exposed to an x-ray beam at 72 having the suggested x-ray beam quality (kV) and x-ray quantity (mAs) values. The actual exposure rate to the patient is then measured at 74. The actual exposure rate is then integrated at 76 to determine the total exposure which is compared to the predicted exposure rate at 78. The compared value is then used to determine if the exposure of the patient is within a predetermined tolerance. If the compared value is not within the predetermined tolerance at 80, then the exposure is continued at 82. However, if the compared value is Within the predetermined tolerance at 80, then the actual patient size is computed at 84. The patient size is computed by using the brightness function for the imaging system which is defined as the function of kV, mAs, and the patient size. Thus, if the brightness, kV, and mAs values are known, then the patient size can be computed. Since the brightness rate (i.e., exposure rate), kV, and mAs values are known, then the patient size can be computed Then the computed actual patient size is used to determine a new x-ray beam quality value (kV) at 86. The new x-ray beam quality value (kV) is determined by using a look-up table containing suggested values for adjusting kV given the initial kV, mAs, and patient size values. Thus, if the initial kV, mAs, and actual patient size are known, then the look-up table will generate a suggested new kV value. The exposure of the patient is adjusted according to the new x-ray beam quality value (kV) and the exposure is continued at 88. The total exposure to the patient is then determined at 90. The total exposure is then compared to a predetermined threshold value at 92. If the total exposure is less than the predetermined threshold, then the exposure is continued at 88. Steps 88-92 continue until the total exposure equals the predetermined threshold. Once the total exposure equals the predetermined threshold then the exposure is continued at 82 and the image on the film is later recorded. In an alternative embodiment, instead of continuing exposure at 88 after the decision at 92, it is possible to go to either the decision at 80 or to compute the patient size at 84.

Figure 6:
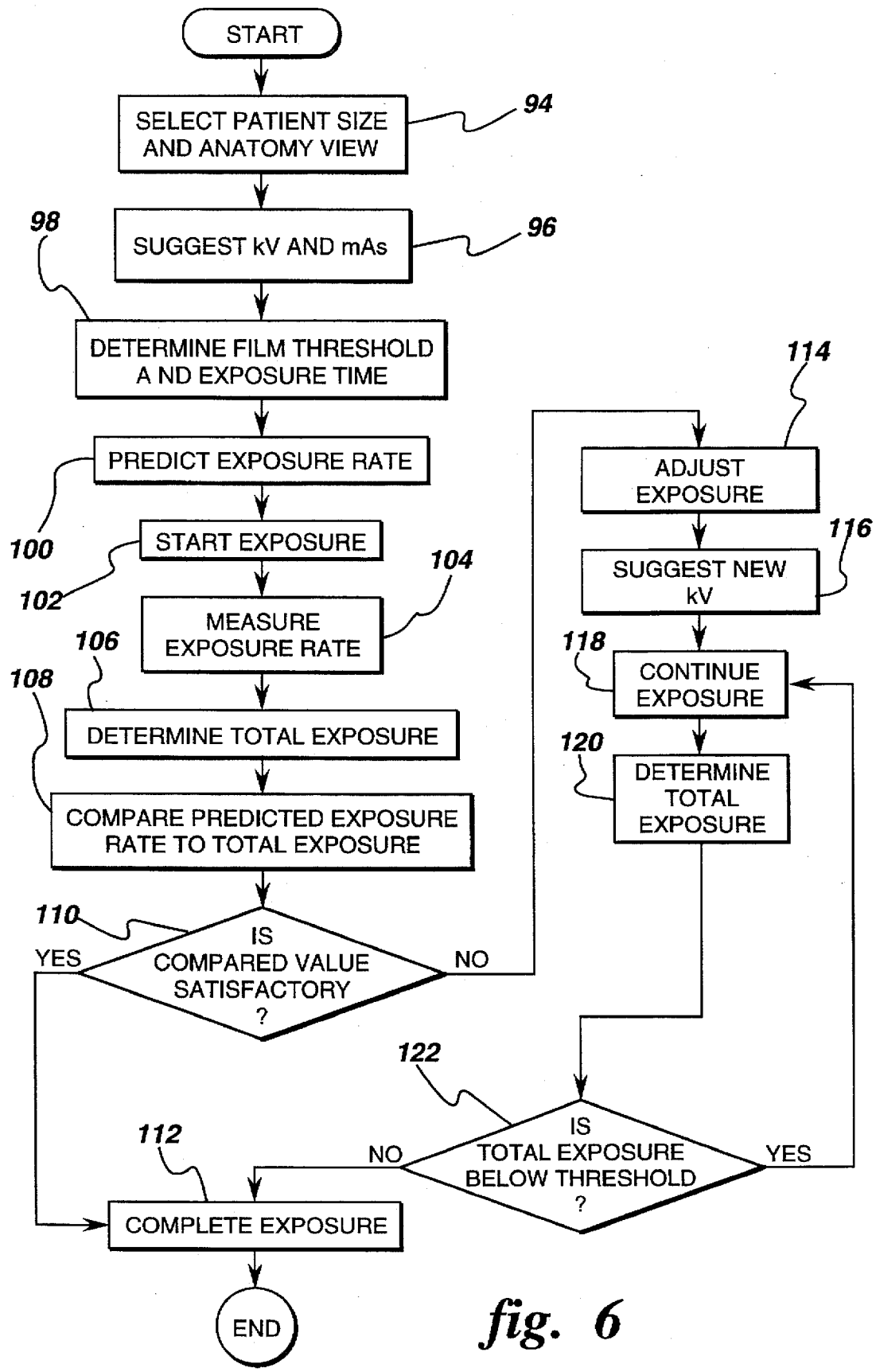
FIG. 6 is a flow chart describing the operation of correcting erroneous exposures according to another embodiment.

A second embodiment of correcting erroneous exposures is set forth in the flow chart of FIG. 6. In the second embodiment, the operation is initiated at 94 where the radiologist or x-ray technician selects the anatomic view to be imaged and estimates the size of the patient. An illustrative list of possible anatomic views for different parts of the body is shown in FIG. 2. After the anatomic view and patient size has been selected an exposure guide table such as the one in FIG. 2 is used at 96 to suggest a value for the beam quality (kV) and the amount of x-rays (mAs). At 98, the film threshold (i.e., brightness) and exposure time is determined. Next, the predicted exposure rate is determined at 100 by dividing the brightness by the exposure time. The patient is then exposed at 102 to an x-ray beam having the suggested x-ray beam quality (kV) and x-ray quantity (mAs) values. The actual exposure rate exposed to the patient is then measured at 104. The actual exposure rate is then integrated at 106 to determine total exposure which is compared to the predicted exposure rate at 108. The compared value is then used to determine if the patient is being exposed at a correct level. If the compared value is satisfactory at 110, then the exposure is completed at 112. However, if the compared value is not satisfactory at 110, then the exposure is adjusted at 114 and a new x-ray beam quality value (kV) is suggested at 116. The new x-ray beam quality value (kV) is suggested by using a look-up table as previously described to suggest a new x-ray quality value from the anatomical view and the predicted and actual exposure rates. More specifically, the selected anatomical view is used to index a row of the table. Each row represents a pairwise association from exposure rate to x-ray quality (kV). The actual exposure rate is located in the table, giving a suggested x-ray quality value, then interpolation may be used if a more precise solution is needed. In addition to using a look-up table it is within the scope of the present invention to use other mechanisms such as fuzzy logic and empirical curve fitting. After locating a new x-ray quality value, the exposure is continued at 118. The total exposure to the patient is then determined at 120. The total exposure is then compared to a predetermined threshold value at 122. If the total exposure is less than the predetermined threshold, then the exposure is continued at 118. Steps 118-122 continue until the total exposure equals the predetermined threshold. Once the total exposure equals the predetermined threshold then the exposure is completed at 112 and the image on the film is later recorded.

The present invention has disclosed a procedure for detecting erroneous exposures that arise because of operator errors such as misalignment or setting errors. By detecting some of the incorrect exposures before completion, and aborting them before completed, patients will receive fewer x-rays, operating costs will decrease, while patient care will improve due to faster diagnosis, less repositioning, and increased availability. In addition to detecting erroneous exposures, the present invention has disclosed a mechanism for improving image quality by correcting erroneous exposures. In particular, the present invention improves image quality by controlling the exposure rate as well as the total exposure through modifications to the x-ray beam quality and x-ray beam quantity values.

It is therefore apparent that there has been provided in accordance with the present invention, a method and system for detecting and correcting an erroneous exposure generated during x-ray imaging that fully satisfy the aims and advantages and objectives hereinbefore set forth. The present invention has been described with reference to several embodiments, however, it will be appreciated that variations and modifications can be effected by a person of ordinary skill in the art without departing from the scope of the invention. For example, it is within the scope of the present invention to use the invention to improve exposures in digital x-ray systems.

The invention claimed is:

1. A method for detecting an erroneous exposure generated during x-ray imaging of a patient, comprising the steps of:

selecting x-ray imaging settings for imaging the patient;
generating x-ray beam quality and x-ray quantity values from the selected x-ray imaging settings;
predicting an exposure rate from the x-ray beam quality and x-ray quantity values, the predicted exposure rate based on x-ray film brightness and exposure time;
exposing the patient to an x-ray beam having the generated x-ray beam quality and x-ray quantity values;
determining a total exposure to the patient;
comparing the total exposure to the predicted exposure rate, resulting in a compared value; and
using the compared value to determine if the patient is being exposed at an erroneous level.

2. The method according to claim 1, wherein the selected x-ray imaging settings comprise an anatomic view and an approximation of size of the patient.

3. The method according to claim 1, further comprising the step of stopping the exposure if the patient is being exposed at an erroneous level.

4. The method according to claim 1, wherein the step of using the compared value to determine if the patient is being exposed at an erroneous level comprises comparing the compared value to a predetermined tolerance.

5. The method according to claim 4, further comprising the step of comparing the total exposure to a predetermined threshold.

6. The method according to claim 5, wherein the exposure is continued until the total exposure is less than the predetermined threshold value.

7. A system for detecting an erroneous exposure generated during x-ray imaging of a patient, the system comprising:

means for selecting x-ray imaging settings for imaging the patient;
means for generating x-ray beam quality and x-ray quantity values from the selected x-ray imaging settings;
means for predicting an exposure rate from the x-ray beam quality and x-ray quantity values, the predicted exposure rate based on x-ray film brightness and exposure time;
an x-ray tube for exposing the patient to an x-ray beam having the generated x-ray beam quality and x-ray quantity values;
a sensor for measuring an actual exposure rate of the patient;
means for determining total exposure from the actual exposure rate;
means for comparing the total exposure to the predicted exposure rate, resulting in a compared value; and
means for using the compared value to determine if the patient is being exposed at an erroneous level.

8. The system according to claim 7, wherein the selected x-ray imaging settings comprise an anatomic view and an approximation of size of the patient.

9. The system according to claim 7, further comprising means for stopping the exposure if the patient is being exposed at an erroneous level.

10. The system according to claim 7, wherein the using means comprises means for comparing the compared value to a predetermined tolerance.

11. The system according to claim 7, wherein the using means comprises means for comparing the total exposure to a predetermined threshold.

12. The system according to claim 11, wherein the exposure is continued until the total exposure is less than the predetermined threshold value.

13. A method for correcting an erroneous exposure generated during x-ray imaging of a patient, comprising the steps of:

selecting x-ray imaging settings for imaging the patient;
generating x-ray beam quality and x-ray quantity values from the selected x-ray imaging settings;
predicting an exposure rate from the x-ray beam quality and x-ray quantity values;
exposing the patient to an x-ray beam having the generated x-ray beam quality and x-ray quantity values;
determining a total exposure of the patient;
comparing the total exposure to the predicted exposure rate, resulting in a compared value;
using the compared value to determine if the patient is being exposed at a correct level;
stopping the exposure if the patient is being exposed at an incorrect level; and
suggesting a new x-ray quality value if the patient is being exposed at an incorrect level, wherein the suggested new x-ray quality value is based on the actual size of the patient determined from the total exposure.

14. The method according to claim 13, wherein the selected x-ray imaging settings comprise an anatomic view and an approximation of size of the patient.

15. The method according to claim 13, further comprising the step of adjusting the exposure of the patient according to the new x-ray quality value.

16. The method according to claim 13, wherein the step of suggesting a new x-ray quality value comprises using a table having new x-ray quality values corresponding to the predicted and total exposure rates.

17. A system for correcting an erroneous exposure generated during x-ray imaging of a patient, the system comprising:

means for selecting x-ray imaging settings for imaging the patient;
means for generating x-ray beam quality and x-ray quantity values from the selected x-ray imaging settings;
means for predicting an exposure rate from the x-ray beam quality and x-ray quantity values;

an x-ray tube for exposing the patient to an x-ray beam having the generated x-ray beam quality and x-ray quantity values;

a sensor for measuring an actual exposure rate of the patient;

means for determining a total exposure from the actual exposure rate;

means for comparing the total exposure to the predicted exposure rate, resulting in a compared value;

means for using the compared value to determine if the patient is being exposed at a correct level;

means for stopping the exposure if the patient is being exposed at an incorrect level; and means for suggesting a new x-ray quality value if the patient is being exposed at an incorrect level, wherein the suggested new x-ray quality value is based on the actual size of the patient determined from the total exposure.

18. The system according to claim 17, wherein the selected x-ray imaging settings comprise an anatomic view and an approximation of size of the patient.

19. The system according to claim 17, further comprising means for adjusting the exposure of the patient according to the new x-ray quality value.

20. The system according to claim 17, wherein the suggesting means comprises a table having new x-ray quality values corresponding to the predicted and total exposure rates.

* * * * *